United States Patent [19]

Bischoff et al.

[11] 4,167,867
[45] Sep. 18, 1979

[54] ACCELERATED STABILITY APPARATUS

[75] Inventors: Dennis E. Bischoff; Gary R. Dickinson; Michael E. Hinshaw; Robert M. Brooker, all of Indianapolis, Ind.

[73] Assignee: The Dow Chemical Company, Midland, Mich.

[21] Appl. No.: 922,010

[22] Filed: Jul. 3, 1978

[51] Int. Cl.$^2$ ............................................. G01N 25/00
[52] U.S. Cl. .................................................. 73/15 R
[58] Field of Search ...................... 73/15 R, 53, 61.1 C

[56] References Cited
U.S. PATENT DOCUMENTS

| | | | |
|---|---|---|---|
| 3,314,282 | 4/1967 | Stiefel | 73/15 |
| 3,574,549 | 4/1971 | Eggertsen | 23/230 |
| 3,670,561 | 6/1972 | Hundere | 73/15 |
| 3,751,985 | 8/1973 | Knedel et al. | 73/15 |
| 3,847,546 | 1/1974 | Paul | 73/61.1 |
| 3,918,913 | 11/1975 | Stevenson et al. | 23/259 |
| 3,960,003 | 6/1976 | Beyer et al. | 73/61.1 |

Primary Examiner—Herbert Goldstein
Attorney, Agent, or Firm—James W. Ambrosius

[57] ABSTRACT

An apparatus for testing the stability of a liquid composition comprising a thermal means, one or more liquid sample chambers, one or more reservoirs for a standard solution, a first flow path for extracting a metered quantity of liquid, a second flow path for extracting a metered quantity of standard solution, and valving means for forming said first and second flow paths.

5 Claims, 1 Drawing Figure

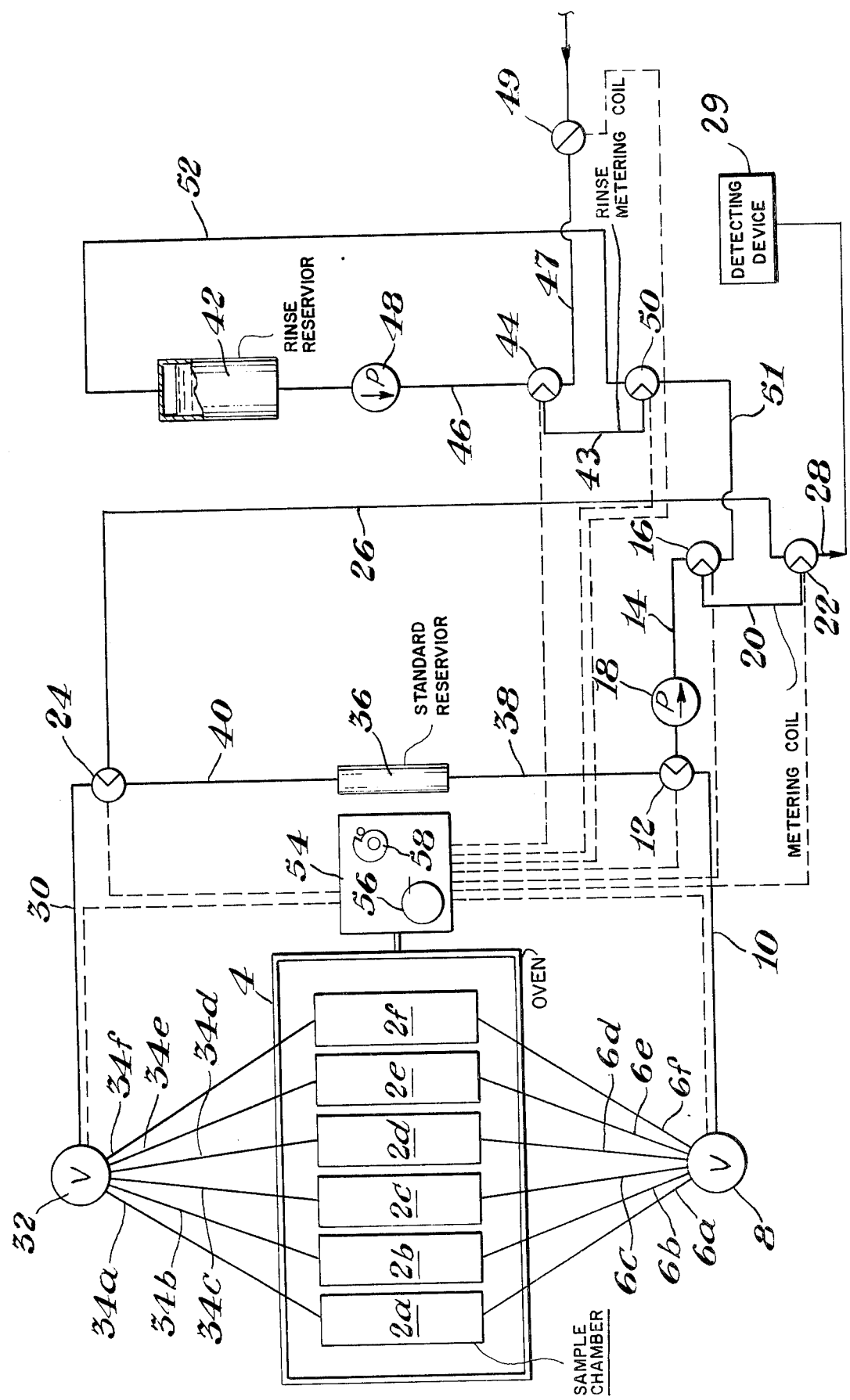

ACCELERATED STABILITY APPARATUS

FIELD OF INVENTION

This invention relates to a thermal, programmed accelerated stability apparatus for laboratory testing chemicals, biologicals, pharmaceuticals, diagnostic products, and the like.

BACKGROUND OF THE INVENTION

Many synthetic and natural products will deteriorate in quality with the passage of time. In products such as pharmaceuticals and diagnostic products where the utility of the product may be impaired by the physical and chemical changes that occur with aging, stability testing becomes an essential part of product development. Stability testing requires that samples of product be collected at predetermined time intervals and analyzed for changes in their chemical and physical makeup. Changes which occur gradually over long time periods often will be speeded up under increased temperature. Therefore, it is possible to shorten the overall time required for stability testing by increasing the temperature that the product is exposed to according to a predetermined program. Even using accelerated stability procedures, sampling and monitoring the product samples requires a substantial amount of operator work time.

SUMMARY OF THE INVENTION

The present invention relates to an automated apparatus for use with an analytical detecting means capable of determining changes in a liquid composition as compared to a standard. The apparatus comprises at least one sample chamber for containing the liquid composition; thermal means for subjecting the liquid composition to a pre-selected temperature; at least one reservoir for standard solution; a first flow path connecting the sample chamber to a metered vessel of known volume for removing a metered sample from the liquid composition exposed to the thermal means by circulating the sample through the metered vessel, whereby the metered vessel is filled to capacity and the excess liquid composition is returned to its point of origin; a second flow path connecting the standard reservoir to a metered vessel of known volume for removing a metered sample from the reservoir containing the standard solution by circulating the standard solution through the metered vessel, whereby the metered vessel is filled to capacity and the excess standard solution is returned to its point of origin; valving means for selectively forming the first and second flow paths and for forming communication between a detecting means or collecting means and the first and second flow paths, respectively; means for rinsing the metered samples of liquid compositions and standard solutions from the first and second flow paths into the detecting means or collecting means; and means for moving the liquid composition and standard solution along the first and second flow paths, respectively.

The valving means of the apparatus described above may be manually operated or, alternatively, the operation of the valves may be automated by incorporating a electrically operated timer and control device, hereafter refered to as a programmer, into the system. The thermal means may also be programmed to change the temperature applied to the liquid composition according to a preselected schedule. By varying the temperature of the thermal means according to a predetermined cycle, accurate determinations of actual expected shelf life for a product may be readily determined. The apparatus may be used in combination with various detecting devices capable of carrying out a number of basic analytical techniques such as for example gas chromatography, liquid chromatography, various types of spectrophotometry, and pH or selective ion electrode determinations.

In one embodiment of the invention the apparatus interfaces directly with the analytical instrument used to analyze both the sample and the standard. The apparatus may also be adapted to merely collect and hold the samples until they are retrieved by an operator. In the latter setup, the analysis is carried out independently of the operation of the apparatus. This may be desirable where some manual operations are required during analysis or where the samples are sent to a different location for analysis.

BRIEF DESCRIPTION OF THE DRAWING

The FIGURE is a schematic representation of the apparatus embodying the present invention.

DESCRIPTION OF PREFERRED FORM OF INVENTION

Referring now to the FIGURE of the drawing, six samples chambers 2a, 2b, 2c, 2d, 2e and 2f are located in a temperature controlled over 4. Each individual sample chamber 2a, 2b, 2c, 2d, 2e and 2f is connected via separate efflux conduits 6a, 6b, 6c, 6d, 6e and 6f to a six port valve 8 having a single sample output conduit 10 connected to three way valve 12. Fluid conduit 14 connects one port of three way valve 12 to a first metering valve 16. A pump 18 is interposed along fluid conduit 14 between three way valve 12 and the first metering value 16. A metering coil 20 of known volume is connected via its proximal end to said first metering valve 16 and at its distal end to a second metering valve 22. Said second metering valve 22 is connected to three way valve 24 via common return conduit 26. The third port of the second metering valve 22 opens into conduit 28 which leads to a detecting device 29 or to a collection reservoir (not shown). A second port of three way valve 24 connects via sample return conduit 30 to six port valve 32. Six port valve 32 communicates with the sample chambers 2a, 2b, 2c, 2d, 2e and 2f via influx conduits 34a, 34b, 34c, 34d, 34e and 34f respectively. Standard reservoir 36 communicates with three way valves 12 and 24 via standard efflux conduit 38 and standard influx conduit 40, respectively.

Rinse reservoir 42 communicates with the first rinse metering valve 44 via rinse efflux conduit 46. Interposed along rinse efflux conduit 46 is pump 48. A rinse metering coil 43 is connected at its proximal end to said first rinse metering valve 44 and at its distal end to a second rinse metering valve 50. Said second rinse metering valve also connects via its second port with the first metering valve 16 by way of rinse conduit 51. The third port of the second rinse metering valve 50 connects directly to the rinse reservoir 42 via rinse influx conduit 52. The third port of the first rinse metering valve 44 is connected to pressure line 47. Pressure valve 49 is interposed in pressure line 47 between the first rinse metering valve 44 and a pressure supplying means (not shown). Valves 12, 16, 22, 24, 44 and 50 are designed such that at any one time any or all can be closed off or operating to provide connection between any two of the three conduits joined to the valves.

The temperature in the oven 4 is controlled by the programmer 54 which has a temperature recorder 56. The precise temperature is determined by a rotating cam 58 which is cut to increase the temperature with time according to a preselected schedule. The programmer may also contain a microprocessor which controls the operation of the various valves according to a predetermined schedule.

In operation, a liquid composition intended for testing is placed in the sample chamber 2a, 2b, etc. and a standard solution is placed in the standard reservoir 36. After the samples have been subjected to a controlled temperature for a predetermined period of time, six port valves 8 and 32 select the proper sample chamber to be analyzed, as for example chamber 2a. Simultaneously, three way valves 12 and 24 rotate to form communications between sample output conduit 10 and fluid conduit 14 and between common return conduit 26 and sample return conduit 30, respectively. With the rotation of the first and second metering valves 16 and 22 to form communication between the metering coil 20 and the fluid conduit 14 and the common return conduit 26, respectively, a complete flow path is formed from the sample chamber 2a through the metering coil 20 and back to the sample chamber. Pump 18 draws the liquid composition out of the sample chamber 2a and around the flow path thus formed. Upon continued rotation of the first and second metering valves 16 and 22 a preselected volume of the fluid composition is held in the metering coil.

In a similar manner first and second rinse metering valves 44 and 50 rotate to form communication between the rinse efflux conduit 46 and the rinse influx conduit 52, thereby forming a complete cycle from the rinse reservoir 42 through the rinse metering coil 43 and back to said rinse reservoir. Thus a third flow path for metering the rinse solution is formed which connects the rinse reservior 42 with the rinse metering coil 48. Upon rotation of the first and second rinse metering valves 44 and 50 to form communication between pressure line 47 and rinse conduit 51, respectively, a metered volume of rinse solution is held in the rinse metering coil 43.

The liquid composition sample held in the metering coil 20 is injected into the detecting device or into a holding vessel via conduit 28. First and second metering valves 16 and 22 rotate to form communication between the rinse conduit 51 and the conduit 28, respectively. Upon alignment of pressure valve 49, pressure line 47 is opened and the metered rinse solution held in the rinse metering coil flows through rinse conduit 51. The metered liquid composition in metering coil 20 is thereby rinsed into conduit 28 and into the detecting device or holding vessel.

The remaining sample chambers 2b, 2c, 2d, 2e and 2f are sampled in the same manner as described for sample chamber 2a above. A sample is extracted from the standard reservoir by the rotation of three way valves 12 and 24 to form communication between the standard efflux conduit and fluid conduit 14 and between the standard influx conduit 40 and common return conduit 26, respectively. In such manner a second flow path is formed, whereby standard solution is circulated from the standard reservoir 36 through the metering coil 20 and back to said standard reservoir. The operation of the other valves for metering the standard solution and forcing it out conduit 28 is identical to the operation described above for the liquid composition samples.

As noted above, the oven temperature is controlled by the programmer 54 which continuously monitors the oven temperature on chart 56. The temperature of the oven is controlled by the rotating cam 58 which raises the temperature of the oven 4 at a preset rate. The optimal rate may be determined mathematically and the cam wheel 58 is cut according to the corresponding equation. To illustrate, the following heating problem has been found to give satisfactory correlation between accelerated stability tests carried out on a liquid composition using the present apparatus and the actual stability of the liquid composition under normal conditions of storage:

$$T = [\text{alpha} \ln(t+1) + \text{beta}]^{-1}$$

wherein:
T = temperature in degrees Kelvin
t = time in days
and for a seven day time cycle starting at 298° K and ending at 353° K.

alpha = $-1.0195 \times 10^{-4}$ beta = $3.356 \times 10^{-3}$

The shelf-life is calculated from the equation $$t = \frac{\ln \frac{C_o}{C}}{K}$$

wherein
$C_o$ is initial concentration of active component
C is the final concentration of active component
K is a constant determined by the Arrhenius equation $$K = \frac{Ae^{-E\#}}{RT}$$

wherein A is the pre-exponential factor (frequency factor) and E# is the activation energy to give the temperature dependence of the rate constant. R is the gas constant and T is the temperature in Kelvin.

In practice E# is determined experimentally.

As noted above, in one preferred embodiment all valves are acuated and controlled by a microprocessor. Other means known to the art for operating the valves could be substituted for the microprocessor, as for example a programmer consisting of a series of cam timers driven by a synchronous motor. The rotating cam in such a programmer is in contact with a linear operated microswitch which is opened or closed by the movement of the cam. The microswitches in turn interface with various other switches and relays that coordinate the operation of the invention by selectively turning the cam motors on and off according to a preselected program of operation.

The apparatus as described above is suitable for testing multiple samples of a single liquid composition. One skilled in the art will recognize that the apparatus is easily adapted to test different liquid compositions by increasing the number of standard reservoirs to provide the standard solutions necessary for comparisons with the liquid compositions intended for analysis. In such an embodiment with multiple standard reserviors, two additional multi-port valves are interposed between the standard reserviors and the three ways valves 12 and 24, respectively.

One skilled in the art will recognize that it would be desirable to have the microprocessor also control the analytical detecting means during the analysis of the samples. In such an embodiment, the individual samples would be automatically fed into the detecting means and analyzed; the microprocessor also would accumulate all data points for each individual sample and calculate the desired results, such as for example shelf life, E#, reaction order, etc.

We claim:

1. An apparatus for testing the stability of a liquid composition by subjecting the liquid composition to a preselected thermal cycle and removing metered volumes of the liquid composition which comprises
   (a) thermal means for subjecting the liquid composition to a pre-selected temperature;
   (b) at least one sample chamber in contact with the thermal means for containing the liquid composition;
   (c) at least one reservoir for containing a standard solution;
   (d) a first flow path connecting the sample chamber to a metered vessel of known volume;
   (e) a second flow path connecting the reservoir for standard solution to a metered vessel of known volume;
   (f) valve means for selectively forming the first and second flow paths and for removing the metered samples from the apparatus for analysis;
   (g) means for rinsing the metered samples from the first and second flow paths;
   (h) and means for moving the liquid composition and standard solution along the first and second flow paths, respectively 2. The apparatus of claim 1 further including analytical detecting means capable of comparing the liquid composition to the standard solution.

3. The apparatus of claim 1 further including a programmer which operates the valve means to form the first and second flow paths according to a pre-selected schedule.

4. The apparatus of claim 1 wherein the temperature of the thermal means is controlled as a function of time according to a pre-selected schedule.

5. The apparatus of claim 1 further including a third flow path for metering the rinse solution which comprises a rinse reservoir connected to a metered vessel of known volume and valve means for forming communication between the metered vessel of said third flow path and the first and second flow paths.

* * * * *